(12) United States Patent
Mathur et al.

(10) Patent No.: US 6,890,514 B2
(45) Date of Patent: May 10, 2005

(54) METHODS FOR DETERMINING RISK OF DEVELOPING CERVICAL CANCER

(75) Inventors: Subbi P. Mathur, Charleston, SC (US); Rajesh S. Mathur, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 28 days.

(21) Appl. No.: 10/182,161

(22) PCT Filed: Jan. 29, 2001

(86) PCT No.: PCT/US01/03009

§ 371 (c)(1),
(2), (4) Date: Jul. 25, 2002

(87) PCT Pub. No.: WO01/54713

PCT Pub. Date: Aug. 2, 2001

(65) Prior Publication Data

US 2003/0017505 A1 Jan. 23, 2003

Related U.S. Application Data

(60) Provisional application No. 60/178,995, filed on Jan. 28, 2000.

(51) Int. Cl.$^7$ .......................... A61K 49/00; C07K 14/00
(52) U.S. Cl. ........................ 424/9.1; 435/7.1; 435/69.6; 435/325; 514/2; 514/12; 530/350
(58) Field of Search ........................ 514/12, 2; 530/350; 435/7.1, 325, 69.6; 424/9.1

(56) References Cited

U.S. PATENT DOCUMENTS

| | | |
|---|---|---|
| 5,591,595 A | 1/1997 | Van Aken et al. |
| 5,679,509 A | 10/1997 | Wheeler et al. |

FOREIGN PATENT DOCUMENTS

| | | |
|---|---|---|
| EP | 0 531080 A2 | 1/1992 |
| WO | WO 98/55872 A | 12/1998 |

OTHER PUBLICATIONS

Blomfield et al., "Can women at risk of cervical abnormality be identified?" *Brit J. of Obstet. Gyn. 105*:486–492 (1998).
Cheng et al., "Translocation of the B Cell Antigen Receptor into Lipid Rafts Reveals a Novel Step in Signaling," *J. Immunol. 166*:3693–3701 (2001).
Choo et al., "Differentiation–independant constitutive expression of the human papillomavirus type 16 E6 and E7 oncogenes in the CaSki cervical tumour cell line," *J. Gen. Virol. 75*:1139–1147 (1994).
Genest et al., "Qualifying the Cytologic Diagnosis of Atypical Squamous Cells of Undetermined Significance Affects the Predictive Value of a Squamous Intraepithellal Lesion on Subsequent Biopsy," *Arch. Pathol. Lab Med. 122*:338–341 (Apr. 1998).

Kihlberg et al., "Characterization of the binding properties of protein LG, an Immunoglobulin–binding hybrid protein," *Eur. J. Biochem 240(3)*:556–563 (1996).
Kim et al., "Regulation of cell growth and HPV genes by exogenous estrogen in cervical cancer cells," *Int. J Gynecol Cancer 10*:157–164 (2000).
Kim et al., "Cervical Cancer with Paraaortic Metastases: Significance of Residual Paraaortic Disease after Surgical Staging," *Gyn. Onc. 69*:243–247 Article No. GO985012 (1998).
Kwack et al., "Functional consequences of the interaction between T–cell antigen receptors and Fc γRs on T cells," *Immunol. Lett. 44(2–3)*:139–143 (1995).
Mathur et al., "Target Antigen(s) in Endometrial Autoimmunity Of Endometriosis," *Autoimmunity 20*:211–222 (1995).
Mathur et al., "Cervical Epidetmal Growth Factor–Receptor (EGF–R) and Serum Insulin–Like Growth Factor II (IGF–II) Levels are Potential Markers for Cervical Cancer," *Am. J. Reproduct. Immunol. 44*:222–230 (2000).
Parker et al., "Cancer Statistics, 1997. " *CA Cancer J. Clin 47*:1–27 (1997).
Steller et al., "Insulin–like growth factor II mediates epidermal growth factor–induced mitogenesis in cervical cancer cells," *Proc. Natl. Acad. Sci. 92*:11970–11974 (1995).
Van Dessell et al., "Serum and Follicular Fluid Levels of Insulin–Like Growth Factor I (IGF–I), IGF–II, and IGF–Binding Protein–1 and –3 During the Normal Menstrual Cycle," *J. Clin. End. Metab. 81(3)*:1224–1231 (1996).
Sun et al., "Different HPV16 E6/E7 Oncogne Expression Patterns in Epithelia Reconstructed from HPV16–immortalized Human Endocervical Cells and Genital Keratinocytes", Oncogene, vol. 15, No. 20, Nov. 1997, pp. 2399–2408.
Park et al., "HPV–16–Related Proteins as the Serologic Markers in Cervical Neoplasia", Gynecologic Oncology, vol. 69, No. 1, Apr. 1998, pp. 47–55.
Marthur et al., "Human Papilloma Virus (HPV)–E6/E7 and Epidermal Growth Factor Receptor (EGF–R) Protein Levels in Cervical Cancer and Cervical Intraepithelial Neoplasia (CIN), American Journal of Reproductive Immunology, Vo. 46, No. 4, Oct. 2001, pp. 280–287.

*Primary Examiner*—Christopher S. F. Low
*Assistant Examiner*—Chih-Min Kam
(74) *Attorney, Agent, or Firm*—Needle & Rosenberg, P.C.

(57) ABSTRACT

The present invention relates generally to a method of identifying a subject having an increased risk of developing cervical cancer based on levels of IGF-II in serum and levels of EGF-R and HPV-E6/E7 in cervical epithelial cells and in serum.

3 Claims, 5 Drawing Sheets

METHODS FOR DETERMINING RISK OF DEVELOPING CERVICAL CANCER

The present application is a 35 U.S.C. §371 national phase application from, and claims priority to, international application PCT/US01/03009, filed Jan. 29, 2001 (published under PCT Article 21(2) in English), which claims priority to U.S. provisional patent application Ser. No. 60/178,995, filed Jan. 28, 2000, which applications are hereby incorporated herein in their entirety.

BACKGROUND OF THE INVENTION

1. Field of the Invention

The present invention relates generally to a method of identifying a subject having an increased risk of developing cervical cancer based on levels of IGF-II in serum and levels of EGF-R and HPV-E6/E7 in cervical epithelial cells and in serum.

2. Background Art

Annual pap smear screening in the USA results in 10 to 15% abnormal cytopathology. For low grade cervical epithelial neoplasia (CIN), the need for treatment in all cases is not clear. The ability to identify patients with CIN who are at greater risk for progression to invasive cancer may allow for more selective treatment protocols, and reduce the number of unnecessary treatments.

Although cytological screening and treatment protocols have already reduced cervical cancer deaths, cervical cancer is still the leading cause of death for women in third world countries. It remains the leading gynecological malignancy in this country with 14,500 new cases and 4,800 deaths every year. (Parker S L, et al, CA Cancer J. Clin. 1997;47:1–27.) About 25% of women with histologically proven high-grade intraepithelial neoplasia are not identified to be at risk during routine gynecological examination. (Blomfield, P I, et al. CBJBrit J Obstet Gyn 1998; 105:486–492; Genest D R, et al.; Arch Pathol Lab Med 1998; 122:338–341.) Although surgical therapy is successful most of the time, metastasis into other locations is hard to diagnose until the cancer is well advanced. This is because the imaging techniques utilized in conjunction with clinical staging fail to reliably identify occult lymphatic spread. (Kim, P Y et al., Gyn Onc 69:243–247; 1998.) The ability to assess patients at risk for metastasis of an invasive cancer would allow the implementation of more appropriate treatment protocols with possible reduction of morbidity and mortality.

The importance of identifying those women with CIN who are at risk for progression into cervical cancer cannot be overemphasized. A rapid cervical tissue or blood test that may help identify those women with CIN who are at risk for developing cervical cancer and help monitor the therapy efficacy will be valuable diagnostic tools. Similarly, a blood test that could identify cervical cancer patients whose cancer was undergoing metastasis.

SUMMARY OF THE INVENTION

The present invention provides a method of identifying a subject having an increased risk of developing cervical cancer, comprising obtaining a test sample of cervical epithelial cells from the subject and a control sample of cervical epithelial cells from an individual known to be free of cervical cancer, determining the amount of HPV-E6/E7 in the test sample and the control sample, and comparing the amount of HPV-E6/E7 in the test sample and the control sample, whereby an amount of HPV-E6/E7 in the test sample that is more than 54% higher than the amount of HPV-E6/E7 in the control sample indicates that the subject has an increased risk of developing cervical cancer.

In another embodiment, the invention provides a method of identifying a subject having an increased risk of developing cervical cancer, comprising obtaining a test sample of cervical epithelial cells from the subject and a control sample of cervical epithelial cells from an individual known to be free of cervical cancer, determining the amount of EGF-R in the test sample and the control sample, and comparing the amount of EGF-R in the test sample and the control sample, whereby an amount of EGF-R in the test sample that is more than 51% higher than the amount of EGF-R in the control sample indicates that the subject has an increased risk of developing cervical cancer.

In another embodiment, the invention provides a method of identifying a subject having an increased risk of developing cervical cancer, comprising obtaining a test sample of serum from the subject and a control sample of serum from an individual known to be free of cervical cancer, determining the amount of IGF-II in the test sample and the control sample, and comparing the amount of IGF-II in the test sample and the control sample, whereby an amount of IGF-II in the test sample that is more than 29% higher than the amount of IGF-II in the control sample indicates that the subject has an increased risk of developing cervical cancer.

In another embodiment, the invention provides a method of assessing the efficacy of a treatment for cervical cancer in a subject, comprising obtaining a first sample of serum from the subject prior to a treatment for cervical cancer, and a second sample of serum following the treatment for cervical cancer, determining the amount of IGF-II in the first sample and the second sample, and comparing the amount of IGF-II in the first sample and the second sample, whereby an amount of IGF-II in the second sample that is lower than the amount of IGF-II in the first sample indicates that the treatment for cervical cancer has been efficacious.

The invention also provides a method of assessing the efficacy of a treatment for cervical cancer in a subject, comprising obtaining a first sample of cervical epithelial cells from the subject prior to a treatment for cervical cancer, and a second sample of cervical epithelial cells following the treatment for cervical cancer, determining the amount of HPV-HPV-E6/E7 in the first sample and the second sample, and comparing the amount of HPV-E6/E7 in the first sample and the second sample, whereby an amount of HPV-E6/E7 in the second sample that is lower than the amount of HPV-E6/E7 in the first sample indicates that the treatment for cervical cancer has been efficacious.

In addition, the invention provides a method of assessing the efficacy of a treatment for cervical cancer in a subject, comprising obtaining a first sample of cervical epithelial cells from the subject prior to a treatment for cervical cancer, and a second sample of cervical epithelial cells following the treatment for cervical cancer, determining the amount of EGF-R in the first sample and the second sample, and comparing the amount of EGF-R in the first sample and the second sample, whereby an amount of EGF-R in the second sample that is lower than the amount of EGF-R in the first sample indicates that the treatment for cervical cancer has been efficacious.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

DETAILED DESCRIPTION OF THE INVENTION

Figure 1A:
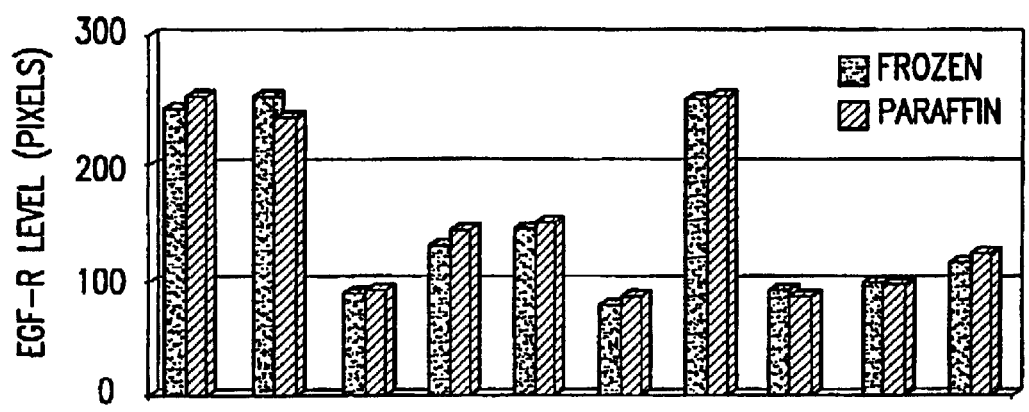
FIGS. 1A and 1B: 1A: Comparison of EGF-R levels in paraffin versus frozen sections of the same cervical biopsies; 1B: Levels of EGF-R in pixels in assays repeated on different days on the same sections
Figure 1B:
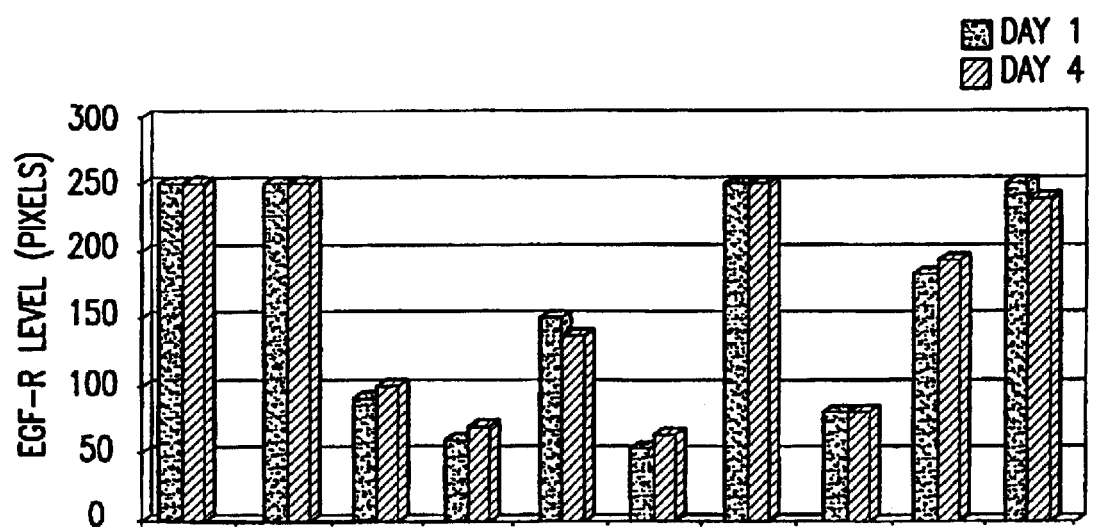

The present invention may be understood more readily by reference to the following detailed description of the preferred embodiments of the invention and the Example included therein.

Before the present methods are disclosed and described, it is to be understood that this invention is not limited to specific compounds and methods, as such may of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. For example, a cell can mean a single cell or more than one cell.

As is mentioned above, there is a great need to identify patients with cervical intraepithelial neoplasia (CIN) who are at a greater risk for progression to invasive cancer. The present invention relates to the unexpected discovery that by comparing the levels of certain proteins in either in serum or in cervical epithelial cells of a subject, to levels of the same protein in serum or in cervical epithelial cells of a population or individuals known not to have cervical cancer, it is possible to identify a subject having an increased risk of developing cervical cancer. The same comparison can also be used following a treatment for cervical cancer to monitor the efficacy of the treatment, or to identify a cervical cancer patient whose cancer is undergoing metastasis or relapse (i.e., recurrence of cervical cancer). The proteins which have been discovered to be correlated to having an increased risk of developing cervical cancer, as well as to the efficacy of treatment for cervical cancer and to metastasis of cervical cancer, are epidermal growth factor receptor (EGF-R), human papilloma virus E6/E7 (HPV-E6/E7), and insulin-like growth factor II (IGF-II). As is shown in Examples 1 and 2, below, the levels of these proteins in either cervical epithelial cells and/or serum also correlate with CIN grading.

Accordingly, the invention provides a method of identifying a subject having an increased risk of developing cervical cancer, comprising obtaining a test sample of cervical epithelial cells from the subject and a control sample of cervical epithelial cells from an individual known to be free of cervical cancer, determining the amount of HPV-E6/E7 in the test sample and the control sample, and comparing the amount of HPV-E6/E7 in the test sample and the control sample, whereby an amount of HPV-E6/E7 in the test sample that is more than 64% higher than the amount of HPV-E6/E7 in the control sample indicates that the subject has an increased risk of developing cervical cancer. In one embodiment, the subject has previously been identified with CIN. Measurements of HPV-E6/E7 in cervical epithelial cells by the methods of the invention also indicate whether the subject has an active HPV infection. In contrast, measurements of HPV mRNA could merely indicate that the subject has had an HPV infection at some point in the past.

In another embodiment, the invention provides a method of identifying a subject having an increased risk of developing cervical cancer, comprising obtaining a test sample of cervical epithelial cells from the subject and a control sample of cervical epithelial cells from an individual known to be free of cervical cancer, determining the amount of EGF-R in the test sample and the control sample, and comparing the amount of EGF-R in the test sample and the control sample, whereby an amount of EGF-R in the test sample that is more than 51% higher than the amount of EGF-R in the control sample indicates that the subject has an increased risk of developing cervical cancer. In one embodiment, the subject has previously been identified with CIN.

Samples of cervical epithelial cells may be cervical specimen sections as well as fresh cervical cell cultures.

Samples of serum can be used as obtained from the body or may undergo standard processing steps.

In another embodiment, the invention provides a method of identifying a subject having an increased risk of developing cervical cancer, comprising obtaining a test sample of serum from the subject and a control sample of serum from an individual known to be free of cervical cancer, determining the amount of IGF-II in the test sample and the control sample, and comparing the amount of IGF-II in the test sample and the control sample, whereby an amount of IGF-II in the test sample that is more than 29% higher than the amount of IGF-II in the control sample indicates that the subject has an increased risk of developing cervical cancer. In one embodiment, the subject has previously been identified with CIN.

Alternatively, in any of the methods described herein that call for comparison to a normal level, the comparison can be to a standard value obtained from a population of subjects known not to have cancer. For example, the values provided herein as controls can be the basis of the comparison, either of absolute measurements or to derive relative values (e.g., percentages). Of course, any method may be used to determine the amount of the relevant protein (HPV-E6/E7, EGF-R, or IGF-II) in the samples, as long as the method specifically and quantitatively measures the amount of the relevant protein in the sample. Methods that have the requisite specificity include methods utilizing antibodies specific for the relevant protein which result in either direct or indirect labeling of the relevant protein. Such methods are well known in the art. (See, e.g., Goding, J. W., Monoclonal Antibodies: Principles and Practice, Academic Press, San Diego Calif. (1986) and Roitt, I., Essential Immunology, Blackwell Scientific Publications, Oxford, UK (1988), both of which are hereby incorporated by reference into this application in their entirety.) As used herein, the term "antibody" refers to polyclonal antibodies, monoclonal antibodies, Fab fragments, F(ab')$_2$ fragments, single chain antibodies, etc.

In a preferred embodiment, levels of the relevant protein are determined in a quantitative immunofluorescent antibody assay. In this assay, the samples are first exposed to a primary antibody directed against the relevant protein. After washing, the samples are exposed to a labeled secondary antibody that binds to the primary antibody, and the relevant protein is then quantitated by measuring the label. Preferably, the secondary antibody is labeled with a fluorescent dye, such as FITC. The intensity of the fluorescence may then be measured by any of the methods known in the art. Preferably, the intensity of immunofluorescence is measured by digitized image analysis, as is described in Example 1. Using this method, the levels of EGF-R, IGF-II, and HPV-E6/E7 may be expressed as pixels.

Accordingly, the invention also provides a method of identifying a subject having an increased risk of developing cervical cancer, comprising obtaining a sample of cervical epithelial cells from the subject, specifically labeling HPV-E6/E7 in the sample with FITC, and measuring the intensity of immunofluorescence in the sample by digitized image analysis, whereby the intensity of immunofluorescence is indicative of the amount of HPV-E6/E7 in the sample, and whereby an amount of HPV-E6/E7 greater than 96 pixels in the sample indicates that the subject has an increased risk of developing cervical cancer.

The invention also provides a method of identifying a subject having an increased risk of developing cervical cancer, comprising obtaining a sample of cervical epithelial cells from the subject, specifically labeling EGF-R in the sample with FITC, and measuring the intensity of immunofluorescence in the sample by digitized image analysis, whereby the intensity of immunofluorescence is indicative of the amount of EGF-R in the sample, and whereby an amount of EGF-R greater than 140 pixels in the sample indicates that the subject has an increased risk of developing cervical cancer.

The invention also provides a method of identifying a subject having an increased risk of developing cervical cancer, comprising obtaining a sample of cervical epithelial cells from the subject, specifically labeling IGF-II in the sample with FITC, and measuring the intensity of immunofluorescence in the sample by digitized image analysis, whereby the intensity of immunofluorescence is indicative of the amount of IGF-II in the sample, and whereby an amount of IGF-II greater than 100 pixels in the sample indicates that the subject has an increased risk of developing cervical cancer.

The levels of the relevant protein may also be measured by well-known ELISA techniques, especially where the samples are serum samples. Thus, the invention also provides a method of identifying a subject having an increased risk of developing cervical cancer, comprising obtaining a serum sample from the subject, and determining the amount of IGF-II in the sample, whereby an amount of IGF-II greater than 670 ng IGF-II per ml of serum indicates that the subject has an increased risk of developing cervical cancer.

As mentioned above, it has also been discovered that the levels of IGF-II, EGF-R, and HPV-E6/E7 in either in serum or in cervical epithelial cells of a subject may be used to monitor the efficacy of a treatment for cervical cancer. For example, as is described in detail in Example 1, below, measurement of IGF-II levels in cervical cancer patients before treatment, less than one year after treatment, and more than one year after treatment, reveals that IGF-II levels drop dramatically immediately after treatment (essentially to the same level of cancer-free controls), but that a wide variation of IGF-II levels are seen greater than one year after treatment. (See Table 3 of Example 1; n.b. the large standard deviation for Group 6, indicating that some patients had very low IGF-II levels while others had very high IGF-II levels.)

Accordingly, the invention also relates to a method of assessing the efficacy of a treatment for cervical cancer in a subject, comprising obtaining a first sample of serum from the subject prior to a treatment for cervical cancer, and a second sample of serum following the treatment for cervical cancer, determining the amount of IGF-II in the first sample and the second sample, and comparing the amount of IGF-II in the first sample and the second sample, whereby an amount of IGF-II in the second sample that is lower than the amount of IGF-II in the first sample indicates that the treatment for cervical cancer has been efficacious.

In another embodiment, the invention relates to a method of assessing the efficacy of a treatment for cervical cancer in a subject, comprising obtaining a test sample of serum from the subject following a treatment for cervical cancer and a control sample of serum from an individual known to be free of cervical cancer, determining the amount of IGF-II in the test sample and the control sample, and comparing the amount of IGF-II in the test sample and the control sample, whereby an amount of IGF-II in the test sample that is less than 29% higher than the amount of IGF-II in the control sample indicates that the treatment for cervical cancer has been efficacious.

In a preferred embodiment, the invention relates to a method of assessing the efficacy of a treatment for cervical cancer in a subject, comprising obtaining a serum sample from the subject, and determining the amount of IGF-II in the sample, whereby an amount of IGF-II less than 670 ng IGF-II/ml serum in the sample indicates that the treatment for cervical cancer has been efficacious.

Similarly, as a correlation has been shown by the present invention between levels of HPV-E6/E7 and cervical cancer, the invention provides a method of assessing the efficacy of a treatment for cervical cancer in a subject. Accordingly, the invention provides a method of assessing the efficacy of a treatment for cervical cancer in a subject, comprising obtaining a first sample of cervical epithelial cells from the subject prior to a treatment for cervical cancer, and a second sample of cervical epithelial cells following the treatment for cervical cancer, determining the amount of HPV-HPV-E6/E7 in the first sample and the second sample, and comparing the amount of HPV-E6/E7 in the first sample and the second sample, whereby an amount of HPV-E6/E7 in the second sample that is lower than the amount of HPV-E6/E7 in the first sample indicates that the treatment for cervical cancer has been efficacious.

In another embodiment, the invention provides a method of assessing the efficacy of a treatment for cervical cancer in a subject, comprising obtaining a test sample of cervical epithelial cells from the subject following a treatment for cervical cancer and a control sample of cervical epithelial cells from an individual known to be free of cervical cancer, determining the amount of HPV-E6/E7 in the test sample and the control sample, and comparing the amount of HPV-E6/E7 in the test sample and the control sample, whereby an amount of HPV-E6/E7 in the test sample that is less than 54% higher than the amount of HPV-E6/E7 in the control sample indicates that the treatment for cervical cancer has been efficacious.

In a preferred embodiment, the invention relates to a method of assessing the efficacy of a treatment for cervical cancer in a subject, comprising obtaining a sample of cervical epithelial cells from the subject, specifically labeling HPV-E6/E7 in the sample with FITC, and measuring the intensity of immunofluorescence in the sample by digitized image analysis, whereby the intensity of immunofluorescence is indicative of the amount of HPV-E6/E7 in the sample, and whereby an amount of HPV-E6/E7 less than 96 pixels in the control sample indicates that the treatment for cervical cancer has been efficacious.

Similarly, as a correlation has been shown by the present invention between levels of EGF-R and cervical cancer, the invention provides a method of assessing the efficacy of a treatment for cervical cancer in a subject, comprising obtaining a first sample of cervical epithelial cells from the subject prior to a treatment for cervical cancer, and a second sample of cervical epithelial cells following the treatment for cervical cancer, determining the amount of EGF-R in the first sample and the second sample, and comparing the amount of EGF-R in the first sample and the second sample, whereby an amount of EGF-R in the second sample that is lower than the amount of EGF-R in the first sample indicates that the treatment for cervical cancer has been efficacious.

Accordingly, the invention provides a method of assessing the efficacy of a treatment for cervical cancer in a subject, comprising obtaining a test sample of cervical epithelial cells from the subject following a treatment for cervical cancer and a control sample of cervical epithelial cells from an individual known to be free of cervical cancer, determining the amount of EGF-R in the test sample and the control sample, and comparing the amount of EGF-R in the test sample and the control sample, whereby an amount of EGF-R in the test sample that is less than 51% higher than the amount EGF-R in the control sample indicates that the treatment for cervical cancer has been efficacious.

In a preferred embodiment, the invention provides a method of assessing the efficacy of a treatment for cervical cancer in a subject, comprising obtaining a sample of cervical epithelial cells from the subject, specifically labeling EGF-R in the sample with FITC, and measuring the intensity of immunofluorescence in the sample by digitized image analysis, whereby the intensity of immunofluorescence is indicative of the amount of EGF-R in the sample, and whereby an amount of EGF-R less than 140 pixels in the control sample indicates that the treatment for cervical cancer has been efficacious. As mentioned above, it has also been discovered that the levels of IGF-II, EGF-R, and HPV-E6/E7 in either the serum or in cervical epithelial cells of a subject may be used to identify a cervical cancer patient whose cancer is undergoing metastasis.

Accordingly, the invention provides a method of detecting metastasis of cervical cancer in a subject who has been determined to be cervical cancer free by standard clinical assessment comprising determining the amount of IGF-II in a serum sample from the subject, whereby an amount of IGF-II greater than 29% above normal indicates metastasis of the cervical cancer. In the above method, an amount of IGF-II of greater than 106% above normal (or 453.3 ng/ml) is an even clearer indication of metastasis.

Additionally, it will be clear to the skilled practitioner that if a cervical cancer patient has low to normal levels of IGF-II, EGF-R, or HPV-E6/E7 in her cervical epithelial cells, and/or other clinical indications that her cervical cancer is in remission, but also has elevated levels of IGF-II in her serum, it is likely that the cervical cancer has metastasized. Accordingly, the skilled practitioner will be able to use any of the present methods for measuring levels of IGF-II, EGF-R, and HPV-E6/E7 in cervical tissue, and IGF-II in serum, to determine if levels of IGF-II in serum are elevated (i.e., at lease 29% above normal), while levels of IGF-II, EGF-R, or HPV-E6/E7 in cervical epithelial cells have decreased.

The present invention can also be used to detect relapse or recurrence of cervical cancer in a subject who has undergone treatment for cervical cancer and appears to be cancer-free based on standard clinical criteria. Accordingly, the amount of IGF-II, EGF-R and/or HPV-E6/E7 is determined, and, if elevated above normal, there is a likelihood that the cervical cancer has recurred. In this method the amount of IGF-II, EGF-R or HPV-E6/E7 is indicative of recurrence if it is 29% above normal (345.4 ng/ml), 51% above normal (98.1 pixels) or 54% above normal (78 pixels), respectively. An amount of IGF-II, EGF-R or HPV-E6/E7 of about 106% above normal (453.3 ng/ml) or higher, about 289% above normal (183 pixels) or higher or about 229% (156.7 pixels) or higher, respectively is an even clearer indication of recurrence.

Similarly, it will be clear to the skilled practitioner that if a cervical cancer patient, following treatment for the cervical cancer which has eliminated clinical signs of cervical cancer, including producing low to normal levels of IGF-II, EGF-R, and/or HPV-E6/E7, begins to have elevated levels of IGF-II, EGF-R, or HPV-E6/E7 in her cervical epithelial cells, then it is likely that the cervical cancer has recurred. Accordingly, the skilled practitioner will be able to use any of the present methods for measuring levels of IGF-II, EGF-R, and HPV-E6/E7 to determine if levels of IGF-II, EGF-R, or HPV-E6/E7 have increased following a remission of the cancer.

For the methods described herein, measurement of IGF-II and EGF-R may also be made in inguinal, pelvic, and abdominal nodes. Accordingly, the relative and absolute values provided herein for the determination of efficacy, relapse, and metastasis are also relevant to assays performed on these nodal tissues.

The invention also provides IGF-II, EGF-R, and HPV-E6/E7 amount correlations to the CIN stages identified clinically. Tables 2, 3 and 4 show a correlation of amount ranges (I.S.D.) of EGF-R, IGF-II (in serum) and HPV-E6/E7, respectively, with the clinically determined CIN stage of the patient. Thus, the level of CIN in a subject can be predicted based on the amount of the marker present in the sample from the subject.

Specific examples of units of absolute and relative measurements are provided herein (e.g., pixels, percentages, ng/ml). However, it should be understood that these units are merely exemplary and do not limit the invention to methods in which these particular units are used, or to the particular labels used in the methods set forth. Likewise, there are routine methods known in the art for converting stated units of measurement into other units of measurement. To the extent that these current or later-developed methods apply to the units of measurement used herein, the present invention contemplates their use in identifying the parameters set out herein. Additionally, the data provided herein is subject to alternative statistical analysis known in the art, such that the relative amounts provided herein can vary without altering the core teaching of the correlations provided.

For example, comparing the mean plus 2 standard deviations of the control and the CIN I groups produced values of 29%, 51%, and 54% for IGF-II, EGF-R and HPV-E6/E7, respectively. Alternatively, comparing just the means of control and CIN I groups produced values of 42%, 93% and 60% for IGF-II, EGF-R and HPV-E6/E7, respectively.

The following Examples are set forth so as to provide those of ordinary skill in the art with a complete disclosure and description of how the methods claimed herein performed, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLES

Example 1

Materials and Methods
Study Groups and Samples

The study controls were 20 women who had consistently normal Papanicolau smear. Twenty six women with abnormal Pap smear who underwent colposcopy in Colpo-Clinic and were clinically diagnosed with CIN I, II and III, and twelve women with recently diagnosed cervical cancer, were enrolled into the study before they underwent therapy. We obtained sections of cervical biopsies from 18 controls, 20 women with CIN and 12 women with cervical cancer. Serum samples were obtained from 20 controls, 26 CIN patients, 12 with cervical cancer before therapy, 5 with cervical cancer <1 yr and 9≧1 yr. after therapy. All women signed an informed consent (protocol approved by the Office for Research Risk Protection) before donating blood and/or tissue samples. The clinics at Charleston (60% white, 30% black and 10% Asian or Hispanic) cater to a mixed racial population and hence our studies are not racially biased.

The laboratory was blinded to the clinical diagnosis of the patient until conclusion of testing. We collated the clinical and research data at the end of the study and entered them in a database for statistical evaluation.

Pre-Treatment of Cervical Biopsy Sections

Paraffin sections were deparaffinized by passing the slides through xylene, 100% ethyl alcohol, 90% ethyl alcohol, 80% ethyl alcohol, 70% ethyl alcohol, 50% ethyl alcohol, 10% ethyl alcohol and finally, deionized glass distilled water. The slides were heated for a minute in boiling antigen unmasking solution and washed in phosphate buffered saline. The slides were stored at 80° C. until further use. Frozen sections are stored at −80° C., after fixing them in methanol, acetic acid mixture (3:1 v/v) and washing in cold PBS.

Immunofluorescent Quantification of EGF-R in Cervical Epithelial Cells

The immunofluorescent antibody assay used is described in Mathur S. et al. (Autoimmunity 1995; 20:211–222). We applied a semi-quantitative immunofluorescent antibody assay to enumerate EGF-R levels on the squamous epithelium of cervical tissues. We used an antibody to a region of recombinant EGF-R in the cytoplasmic domain, raised in sheep, as primary antibody (ICN Biomedicals, Lisle, Ill.) and fluorescein isothio cyanate (FITC)-conjugated anti-sheep IgG antiserum (Calbiochem-Novabiochem, Cambridge, Mass.) as the secondary antibody. The intensity of imununofluorescence was measured by digitized image analysis using an Axioplan research microscope (Carl Zeiss Inc., Jena, Germany) equipped with a 100 w mercury light source and a 100× plan-neufluar na1.3 objective. The images were captured with a Dage CCD 100 integrating camera (Dage-MTI, Michigan, Mich., USA) and a Flashpoint 128 Capture Board (Integral Technologies, Indiana, USA). The image capture and processing were done on a Dual Pentium Pro 200 Imaging Workstation (Dell Computers, Texas, USA), using Image-Pro Plus software (Media Cybernetics, Maryland, USA). The settings were left constant through processing of all the images. Cells with maximum positive intensity measured at 250 to 260 pixels and the negative areas measured 50 to 80 pixels. Small areas of squamous epithelial cells were outlined and the fluorescent intensity was assessed in pixels, without bias in each area, until the whole relevant field was covered. We analyzed at least 20 fields for each tissue. Mean values of these observations per microscopic field were obtained using the Image-Pro software. Levels of cervical biopsy EGF-R (expressed as pixels) obtained in each patient were entered in the database for statistical analysis.

Quality Control for Immunofluorescent Antibody Assay

The immunofluorescent assay was performed under well standardized conditions. The following were the measures that were taken to ensure the reliability of the assay: The immunoperoxidase method used by earlier cited studies yields false positive results due to endogenous peroxidase activity. The immunofluorescent antibody assay that we used is very specific and sensitive. The quantification of the fluorescence using state-of-the-art software was an added bonus and lent objectivity to the measurement instead of the subjective +, ++, +++ and − ratings. The immunofluorescent signal was similar in formalin fixed paraffin sections versus methanol-fixed frozen sections of the same tissues. Inter-assay reliability between assays done on different days and intra-assay reliability were ≧95%.

Often, two observers assessed the immunofluorescence, with excellent agreement. We studied hematoxylin-eosin stained sections cut at the same location and marked the areas of interest before we processed the sections for the immunofluorescent studies.

Unlike the homogenous preparations of cervical cancer cell lines, the cervical biopsies offer multiple cell types. However, EGF-R expression was confined to the cervical epithelial cells, being highest in the para-basal, basal and squamous epithelial cells. While quantifying levels of these proteins, we selected only those areas that contained epithelial cells. Stromal and other cells had negligible EGF-R. These cells were not included in our quantification.

The microscopic light intensity was kept constant, so that a range of measurements below the saturation point of about 250 to 260 pixels were obtained. Positive and negative controls were maintained. Addition of anti-fade DABCO ensured the reproducibility of the observations over a period of time.

Figure 2:
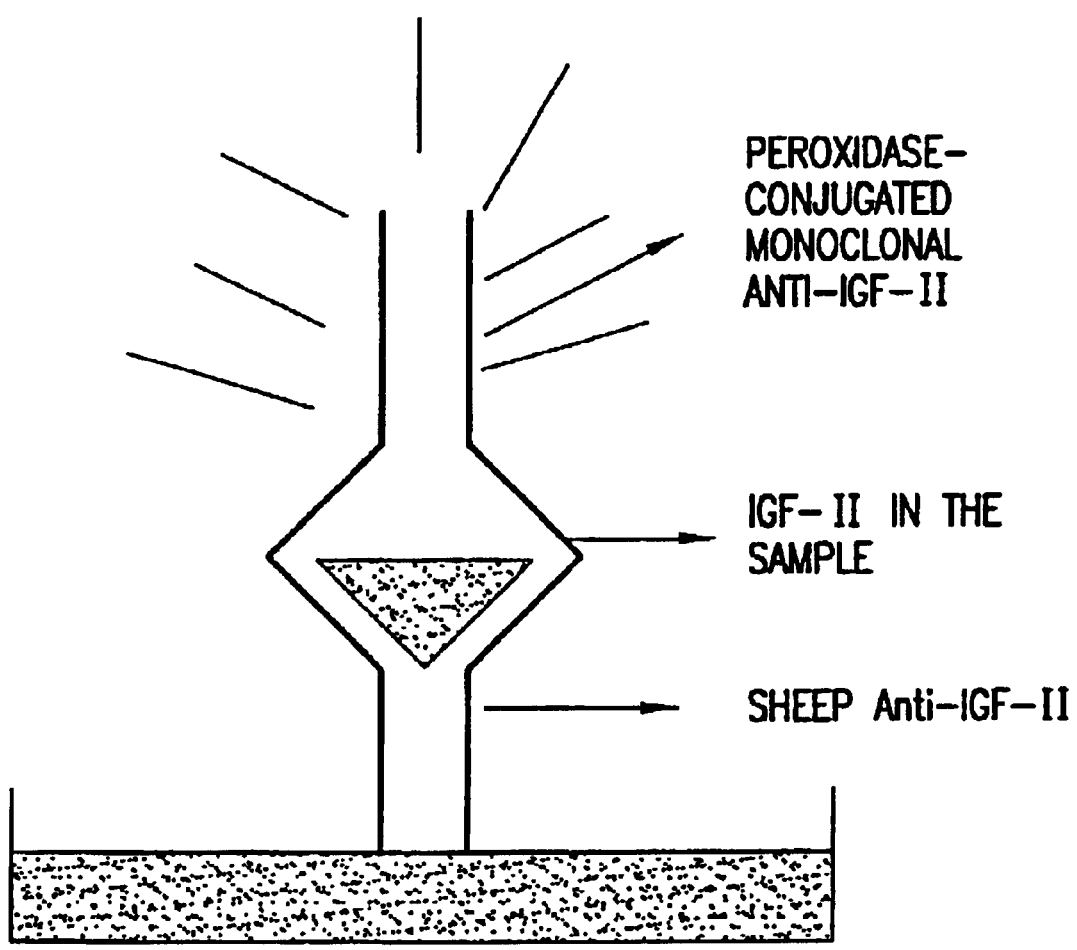
FIG. 2: Principle of the Antigen-capture ELISA for measuring Serum IGF-II Levels.
Figure 3:
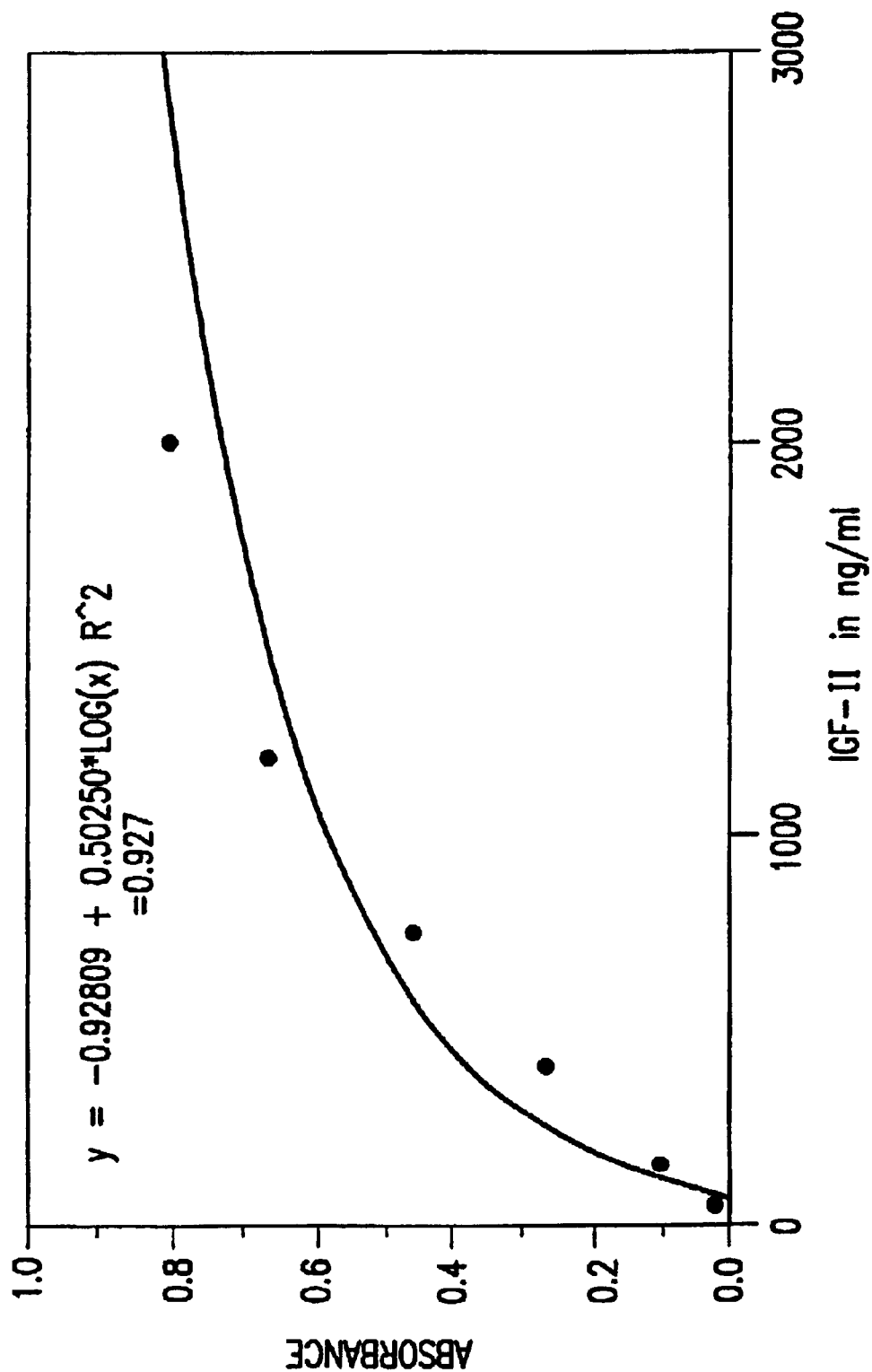
FIG. 3: Standard Curve for measuring IGF-II in Serum

Determination of the Levels of serum IGF-II: A non-extraction IGF-II ELISA kit (DSL-10-2600) from Diagnostics Systems Laboratories, Inc., Webster, was used to determine serum IGF-II levels in our study participants. This is an enzymatically amplified "two step" sandwich-type immunoassay (FIG. 2). (Van Dessell H J H M, et al., J. Clin. End. Metab. 1996;81:1224–1231.) In the assay, eight standards, two low level and high level controls and the unknown samples were incubated in triplicate in microtiter plate wells that have been coated with an anti-IGF-II antibody. After the first incubation for two hours with shaking in an Orbital shaker at room temperature and washing with PBS-Tween solution, the wells were incubated with a second anti-IGF-II antibody raised in a different species and labeled with horseradish peroxidase. After a second incubation for 1 hour with shaking and washing with PBS-Tween, the wells were incubated with the substrate tetra methyl benzidine (TMB). We determined the degree of enzymatic turnover of the substrate by dual wavelength absorbance measurement at 450 and 620 nm. The absorbance measured is directly proportional to the concentration of IGF-II present. A set of IGF-II standards was used to plot a standard curve of absorbance versus IGF-II concentration from which the IGF-II concentrations in the unknown samples were calculated as follows:

We plotted a standard curve using the absorbance values obtained for the standards with the Statworks program. FIG. 3 presents a sample standard curve. To calculate the IGF-II levels in our study samples we followed the following method: If $r^2$ value is 0.927, we multiply Absorbance (y) by 0.927. Let us call this Y.

$$Y = -0.928 + 0.50250 \times \log_X \quad 0.50250 \times \log_X = Y + 0.928$$

$$\log_X = \frac{Y + 0.928}{0.50250};$$

Second log of this value will give the concentration ($x$).

Figure 4A:
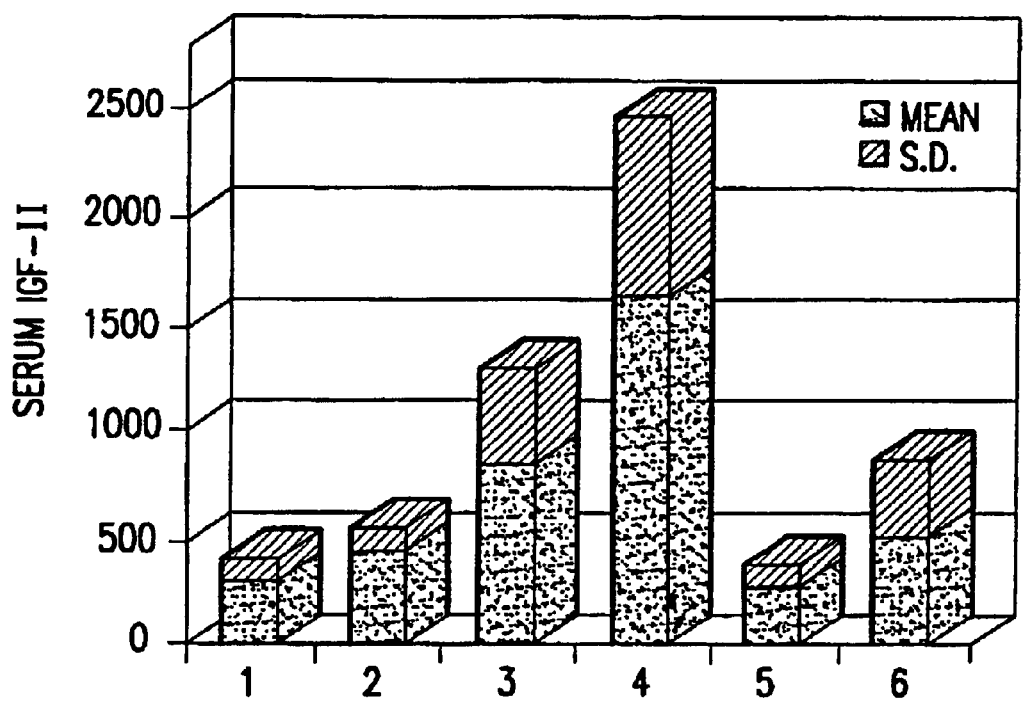
FIGS. 4A and 4B: 4A: Serum levels of IGF-II (mean±S.D. ng/ml) in the Study Groups. 4B: Serum levels of IGF-II in women with cervical cancer >3 and <3 cm in diameter at the time of diagnosis, in post therapy period

We have assessed the reproducibility of the assays by performing the assays on standards and controls provided by the company and by using the same kit on different days, comparing different batches of kits and performing the assays in triplicates. The serum levels of IGF-II in normal women have previously been assessed to be in the range of 375 to 650 ng/ml (n=250 samples) and are known to have minor variations during the menstrual cycle.
Van Dessell H J H M, et al., J. Clin. End. Metab. 1996;81:1224–1231.
Statistics: A Student's 't' test was used to determine the levels of significance of values between the controls and the two patient groups and among the patient groups. Statworks software from Microsoft was employed for this purpose.
Results
Levels of EGF-R in Cervical Epithelial Cells The levels of EGF-R in the cervical squamous epithelial cells of women with cervical cancer were significantly higher than the controls (p<0.001) and women with CIN (p=0.02). The levels of EGF-R were also higher in women with CIN than the controls (p<0.001 for CIN II and III and <0.05 for CIN I; Table 2).
Levels of Serum IGF-II: The controls had the IGF-II levels comparable to the normal levels established so far, using the non-extraction ELISA. [31] Women with cervical cancer had elevated levels of IGF-II that were significantly higher than those of the controls (p<0.001; no overlapping values with the controls), and women with CIN II and III (p<0.05). The women with CIN II and III had significantly higher IGF-II levels than the controls (p=0.03), while the women with CIN I had similar levels to controls (p=NS). Most importantly, however, women with cervical cancer in the post-therapy period had significantly lower serum IGF-II levels than the women with cervical cancer before therapy (p<0.001; Table 3; FIG. 4A).

Figure 4B:
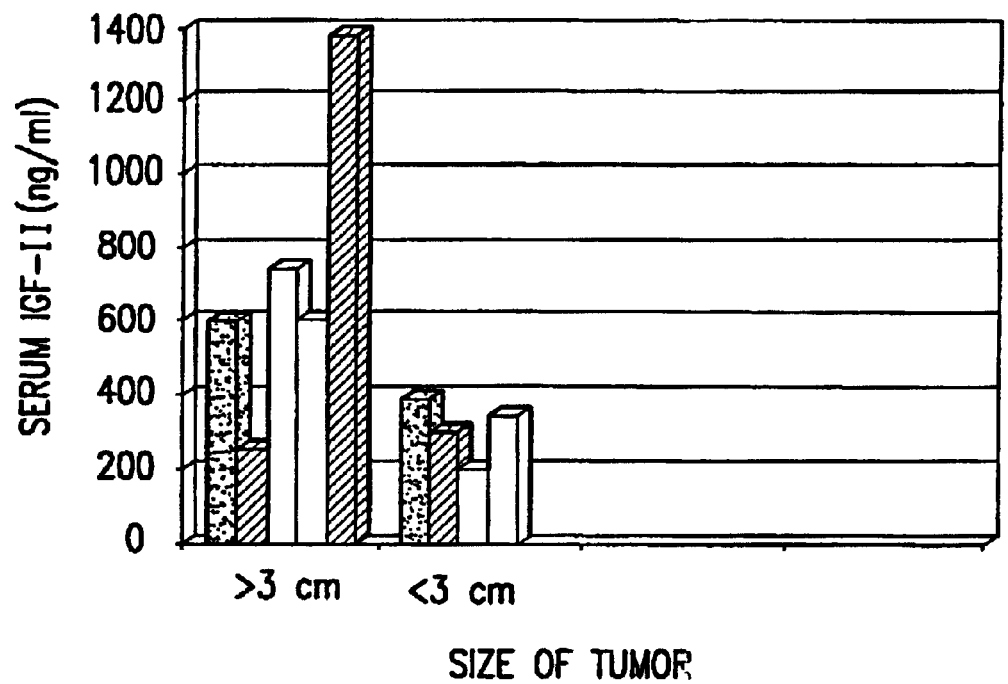

The cut-off positive levels from our control values (Group 1) so far will be the mean+2 SD of IGF-II levels in controls, viz., 520 ng/ml. All 12 women with cervical cancer (Group 4) had IGF-II levels far higher than this cut-off value. Sixteen of 18 (89%) women with CIN II and III (Group 3) had IGF-II levels higher than 520 ng/ml, while only 3 of 5 women with CIN I (Group 2) had significantly high levels. We observed that in groups 5 (<1 year after therapy for cervical cancer) and 6 (≧1 year after therapy for cervical cancer), patients with tumor size of ≧3 cm in diameter (bulky tumors) at the time of diagnosis had significantly higher levels of serum IGF-II than the ones with <3 cm size tumors (FIG. 4B).

One cancer patient, SS, had her blood drawn on three different days. The levels of IGF-II remained similar (2649, 2661 and 2406 ng/ml), confirming the validity of the method being used.
EGF-R and IGF-II Levels: 100 percent of patients with cervical cancer and 77 to 89% of patients with advanced CIN have elevated levels of cervical EGF-R and serum IGF-II. (Table 4).

Example 2

Materials and Methods
Study Subjects

The study was approved by the Medical University of South Carolina Human Research Review Board of the Office for Research Risk Protection. We obtained archival (from the Department of Pathology and Laboratory Medicine) and snap-frozen cervical biopsies from 12 control women, 20 women with CIN I (n=5), II and III and 10 women with cervical cancer. The women in age ranged from late forties to early sixties. There was no racial bias in our selection of study subjects.
Pretreatment of Archival Cervical Biopsy Sections We have standardized the protocol for pre-treating archival tissue sections for use in an objective semi-quantitative immunofluorescent antibody assay for measuring HPV-E6/E7 protein and EGF-R levels (20). Briefly, paraffin sections were deparaffinized by passing the slides through xylene, 100% ethyl alcohol, 90% ethyl alcohol, 80% ethyl alcohol, 70% ethyl alcohol, 50% ethyl alcohol, 10% ethyl alcohol and finally, deionized glass distilled water. The slides were heated for one minute in boiling antigen-unmasking citrate buffer solution and washed in cold phosphate buffered saline. The slides were stored at −80° C. until further use. Frozen sections were stored at −80° C., after fixing them in methanol, acetic acid mixture (3:1 v/v) and washing in cold PBS.
Immunofluorescent Quantification of HPV-E6/E7 and EGF-R in Cervical Epithelial Cells We applied a semi-quantitative immunofluorescent antibody assay to enumerate HPV-E6/E7 and EGF-R levels on the squamous epithelium of cervical tissues. We used an antibody to a region of recombinant EGF-R in the cytoplasmic domain, raised in sheep (ICN Biomedicals, Lisle, Ill.), and monoclonal antibodies to HPV E6 and E7 (Oncogene Research Products, Cambridge, Mass.) as primary antibodies. Fluorescein isothio-cyanate (FITC)-conjugated anti-sheep or anti-mouse IgG antibody (ICN Biomedicals, Lisle, Ill.) was the secondary antibody. Cervical cancer cell lines, known to be negative (HT-3) and positive (CaSki and ME-180) for HPV 16 and 18/39, respectively, were used as controls in the setting up of the assay.

The intensity of immunofluorescence was measured by digitized image analysis using an Axioplan research microscope (Carl Zeiss Inc., Jena, Germany) equipped with a 100 w mercury light source and a 100× plan-neufluar na1.3 objective. The images were captured with a Dage CCD 100 integrating camera (Dage-MTI, Michigan, Mich., USA) and a Flashpoint 128 Capture Board (Integral Technologies, Indiana, USA). The image capture and processing were done on a Dual Pentium Pro 200 Imaging Workstation (Dell Computers, Texas, USA), using Image-Pro Plus software (Media Cybernetics, Maryland, USA). The settings were left constant through processing of all the images. Cells with maximum positive intensity measured 250 to 260 pixels and the negative areas measured 40 to 60 pixels in light intensity. Small areas of squamous epithelial cells were outlined and the fluorescent intensity was assessed in pixels, without bias in each area, until the whole relevant field was covered. Two observers analyzed at least 20 fields for each tissue. Mean values of these observations per microscopic field were obtained using the Image-Pro software. Levels of cervical biopsy EGF-R and HPV-E6/E7 (expressed as pixels) obtained in each patient were entered in the database for statistical analysis. The quality control measures are described above in Example 1.

Statistical Analysis of the Data

Levels of HPV-E6/E7 and EGF-R were compared between the controls, CIN and cervical cancer, using Student's 't' test. Linear regression analysis was done to ascertain the correlation between HPV-E6/E7 and EGF-R. Bonferroni correction for multiple testing was done.

Results

Cell and Tissue Controls for the Immunofluorescent Antibody Assay

HPV-negative HT-3 was negative (40 to 60 pixels per cell), while the other two HPV-positive cell lines were strongly positive (180.7±32.2 pixels per cell in CaSki; 194.5±37.8 pixels per cell in ME 180) for HPV E6 and E7 proteins. The levels of EGF-R in HT-3 cells were lower ($p<0.001$) than those in HPV-positive cell lines.

Figure 5:
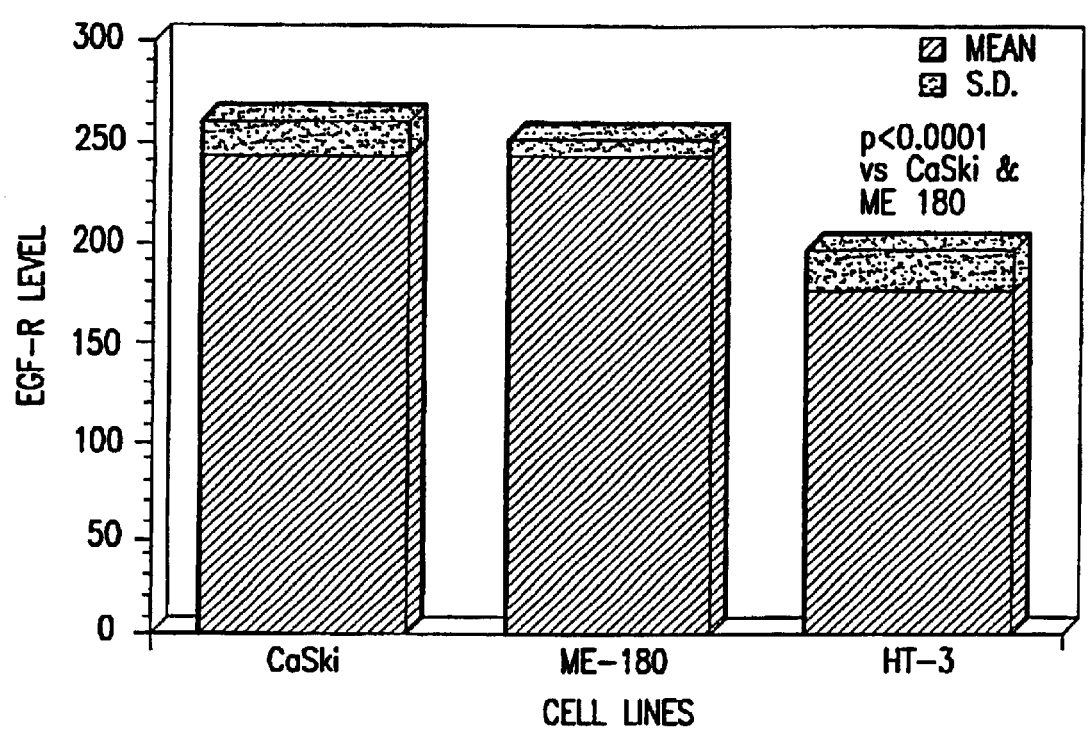
FIG. 5: Levels of EGF-R (in pixels per cell) in the Cervical Cancer Cell Lines.

Paraffin sections of cervical biopsies from women with CIN that were positive for HPV-E6/E7 mRNA (positive controls) showed significant levels of HPV E6 and E7 proteins (FIG. 5). Since HPV-E6/E7 proteins are more related to the high risk HPV 16 and 18 strains, we decided to pool the primary antibodies to HPV-E6 and E7 for further studies.

HPV-E6/E7 and EGF-R are Specific to Epithelial Cells.

The immunofluorescent staining for HPV-E6/E7 and EGF-R proteins was specific to basal, para-basal and squamous epithelial cells, while the stromal and other cells in the archival cervical biopsies of HPV-positive women with cervical cancer or CIN stained negative for both proteins. In a representative patient with cervical cancer, levels of HPV-E6/E7 and EGF-R were elevated in the basal and parabasal cervical epithelial cells and squamous epithelial cells of the cervical cancer. One lymph node from this patient that was histopathologically judged to be normal, was negative for HPV-E6/E7, and was barely positive for EGF-R.

Levels of EGF-R and HPV-E6/E7 in Cervical Biopsies

Levels of HPV-E6/E7 and EGF-R were in the negative range in all controls, 4 of 5 women with CIN I, and 2 of 15 women with CIN II/III. The only exception was a woman with cervical cancer negative for HPV-E6/E7, but positive for EGF-R. Levels of HPV-E6/E7 and EGF-R, specific to para-basal, basal and squamous epithelial cells, were significantly higher in women with advanced CIN and cervical cancer than the controls (Table 5). On the whole, the HPV-E6/E7 and EGF-R levels significantly and positively correlated with each other ($r=18.98$; $p<0.001$, by linear regression analysis).

Cut-off values for positive ranges were calculated as $\geq$ mean values in controls +2 S.D.: HPV-E6/E7: $\geq 63$ pixels; EGF-R: $\geq 81$ pixels.

Throughout this application, various publications are referenced. The disclosures of these publications, and the references cited therein are hereby incorporated by reference in their entireties into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

TABLE 1

Protocol for immunofluorescent enumeration of EGF-R in cervical biopsy sections.

| | Paraffin Sections | Frozen Sections |
|---|---|---|
| Preparation | Deparaffinization followed by incubation in antigen unmasking solution and rehydration. | Fixed in methanol, acetic acid mixture (3:1), washed in cold PBS, followed by cold distilled water. |
| Dilution of Primary Antibody (Anti-EGF-R) raised in sheep or mouse | 1:50 in cold PBS | 1:50 in cold PBS |
| Incubation time | 45 minutes in cold (4° C.) | 45 minutes in cold (4° C.) |
| Washing | 10 minutes in PBS, followed by 1 minute in distilled water | 10 minutes in PBS, followed by 1 minute in distilled water |
| Secondary Antibody Fluorescein-conjugated rabbit anti-sheep IgG | Dilution: 1:50 | Dilution: 1:50 |
| Incubation time | 45 minutes in cold (4° C.) | 45 minutes in cold (4° C.) |
| Washing | 10 minutes in PBS, followed by 1 minute in distilled water | 10 minutes in PBS, followed by 1 minute in distilled water |

TABLE 2

Levels of EGF-R (in pixels) in the Cervical Biopsies of Controls, Women with CIN and Cervical Cancer.

| Study Group | EGF-R Level (mean ± S.D.) | p value Vs Controls (Student's test) |
|---|---|---|
| Controls (n = 18) | 58 ± 11 | — |
| CIN I (n = 3) | 112.3 ± 14.2 | <0.05 |
| CIN II and III (n = 17) | 217.2 ± 33.8 | <0.001 |
| Cervical Cancer (n = 12) | 253.6 ± 11.7 | <0.0001 (0.02 Vs. CIN) |

TABLE 3

Levels of IGF-II in Serum of Controls, Women with CIN and Cervical Cancer and in women with Cervical Cancer <1 yr and >1 yr after Therapy (Highlighted levels are >421 ng/ml (> mean + 2 SD of Controls).

| Category of Patients | Serum IGF-II level (mean ± S.D.) ng/ml | P Value Vs. Controls |
|---|---|---|
| Group 1: Controls (n = 20) | 318.6 + 99.6 | — |
| Group 2: CIN I (n = 8) | 453.1+ 107.7 | N.S. |
| Group 3: CIN II and III (n = 18) | 871.9 + 418.6 | =0.03 |
| Group 4: Cervical Cancer Before Therapy (n = 12) | 1642.3 + 835.9 | <0.001 |
| Group 5: Cervical Cancer <1 yr. After Therapy (n = 5) | 2902.2 + 82.6 | N.S.; p < 0.001 Vs Group 4 |
| Group 6: Cervical Cancer >1 yr. After Therapy (n = 9) | 532.9 + 346.7 | N.S.; p < 0.001 Vs Group 4 |

TABLE 4

Number of Patients with CIN and Cervical Cancer with elevated Levels of Cervical EGF-R and Serum IGF-II Levels (>Mean + 2 SD controls).

| Criteria | Controls | % | CIN-I | % | CIN II & III | % | Cervical Cancer | % |
|---|---|---|---|---|---|---|---|---|
| EGF-R levels | 0/20 | 0 | 1/3 | 33 | 13/17 | 77 | 12/12 | 100 |
| Serum IGF-II levels | 0/20 | 0 | 3/5 | 60 | 16/18 | 89 | 12/12 | 100 |

TABLE 5

Levels of HPV-E6/E7 and EGF-R (in Pixels) in the study groups

| Category* | HPV-E6/E7 Level (Pixels) Mean ± S.D. | P Value Vs. Controls | EGF-R Level (Pixels) Mean ± S.D. | P Value Vs. Controls |
|---|---|---|---|---|
| Controls (n = 12) | 52.5 ± 5.0 | — | 70.4 ± 5 | — |
| CIN-I (n = 5) | 84.0 ± 6.0 | 0.05 | 101 ± 10 | <0.05 |
| CIN II and III (n = 15) | 194.5 ± 37.8 | <0.001 | 235 ± 40 | <0.001 |
| Cervical Cancer (n = 10) | 180.7 ± 32.2 | <0.001 | 199 ± 20 | <0.001 |

*All Controls, 4 of 5 women with CIN I, 1 to 15 women with CIN II/III and 1 of 10 women with cervical cancer were negative for HPV E6/E7. Cut-off values for positive ranges are calculated as ≥ means control values + 2 S.D.: HPV-E6/E7: ≥ 63 pixels; EGF-R: ≥ 81 pixels

What is claimed is:

1. A method of determining whether a subject has an increased risk of developing cervical cancer, comprising determining the amount of Insulin-like Growth factor-II (IGF-II) in a serum sample from the subject, whereby the amount of IGF-II greater than 29% above normal control value indicates that the subject has an increased risk of developing cervical cancer.

2. The method of claim 1, wherein the subject has previously been identified as having cervical intraepithelial neoplasia (GIN).

3. A method of assessing the efficacy of a treatment for cervical cancer in a subject, comprising determining the amount of Insulin-like Growth factor-II (IGE-IL) in a serum sample from the subject, whereby the amount of IGF-II less than 29% above normal control value indicates that the treatment for cervical cancer has been efficacious.

* * * * *

UNITED STATES PATENT AND TRADEMARK OFFICE
CERTIFICATE OF CORRECTION

PATENT NO. : 6,890,514 B2
DATED : May 10, 2005
INVENTOR(S) : Mathur et al.

It is certified that error appears in the above-identified patent and that said Letters Patent is hereby corrected as shown below:

Column 15,
Line 29, replace "2902.2" with -- 290.2 --.

Column 16,
Line 40, replace "(GIN)" with -- (CIN) --.
Line 43, replace "(IGE-IL)" with -- (IGF-II) --.

Signed and Sealed this

Twenty-third Day of August, 2005

JON W. DUDAS
*Director of the United States Patent and Trademark Office*